(12) United States Patent
Moya et al.

(10) Patent No.: US 10,130,305 B2
(45) Date of Patent: Nov. 20, 2018

(54) DEVICE AND METHODS FOR AUTOMATED TESTING

(71) Applicant: Under Armour, Inc., Baltimore, MD (US)

(72) Inventors: Rogelio Moya, Austin, TX (US); Michael Voth, Austin, TX (US); Pedro Feitosa, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 142 days.

(21) Appl. No.: 15/135,771

(22) Filed: Apr. 22, 2016

(65) Prior Publication Data

US 2017/0308663 A1   Oct. 26, 2017

(51) Int. Cl.
| | |
|---|---|
| *A61B 5/00* | (2006.01) |
| *G16H 40/63* | (2018.01) |
| *A63B 22/02* | (2006.01) |
| *G16H 20/30* | (2018.01) |
| *G06F 19/00* | (2018.01) |
| *A61B 5/024* | (2006.01) |
| *A61B 5/11* | (2006.01) |

(52) U.S. Cl.
CPC ............ *A61B 5/681* (2013.01); *A61B 5/0022* (2013.01); *A61B 5/0024* (2013.01); *A61B 5/6803* (2013.01); *A61B 5/6807* (2013.01); *A61B 5/6898* (2013.01); *A63B 22/02* (2013.01); *G06F 19/00* (2013.01); *G16H 20/30* (2018.01); *G16H 40/63* (2018.01); *A61B 5/02438* (2013.01); *A61B 5/1118* (2013.01); *A61B 5/4806* (2013.01); *A61B 5/7278* (2013.01); *A61B 2562/0219* (2013.01)

(58) Field of Classification Search
CPC .......................... A61B 5/0024; G06F 19/3418
USPC ..................................................... 340/870.07
See application file for complete search history.

(56) References Cited

U.S. PATENT DOCUMENTS

| | | |
|---|---|---|
| 8,700,354 B1 | 4/2014 | Bentley et al. |
| 8,702,516 B2 | 4/2014 | Bentley et al. |
| | (Continued) | |

FOREIGN PATENT DOCUMENTS

| | | |
|---|---|---|
| CN | 102609341 | 7/2012 |
| DE | 10107134 | 8/2002 |
| | (Continued) | |

*Primary Examiner* — Fabricio R Murillo Garcia (57) ABSTRACT

A testing device which provides testing relating to a health parameter monitoring device and/or a health monitoring application run at a user device is disclosed. In one embodiment, the device comprises: a transceiver which receives a control signal from a controlling device; a health parameter monitoring device connection port which connects to the health parameter monitoring device; a user device connection port which connects to the user device; and a plurality of simulation apparatus configured to electronically recreate one or more physiological parameters of a user according to the control signal. The physiological parameters are monitored by the health parameter monitoring device, which provides a plurality of data relating thereto to the user device for entry within the health monitoring application. The user device outputs at least a display of the health monitoring application to the controlling device for analysis thereof. Systems and methods for performing testing are also provided.

20 Claims, 5 Drawing Sheets

(56) References Cited

U.S. PATENT DOCUMENTS

| | | | |
|---|---|---|---|
| 8,827,824 B2 | 9/2014 | Bentley et al. | |
| 8,903,521 B2 | 12/2014 | Goree et al. | |
| 8,941,723 B2 | 1/2015 | Bentley et al. | |
| 8,944,928 B2 | 2/2015 | Kaps et al. | |
| 9,039,527 B2 | 5/2015 | Bentley et al. | |
| 9,237,070 B2 | 1/2016 | Hill et al. | |
| 2004/0073464 A1* | 4/2004 | Huang | A61B 5/0002 705/3 |
| 2006/0179363 A1 | 8/2006 | Labanca et al. | |
| 2007/0276197 A1* | 11/2007 | Harmon | G06F 19/00 600/300 |
| 2008/0028396 A1 | 1/2008 | Stich et al. | |
| 2009/0054737 A1* | 2/2009 | Magar | A61B 5/0205 600/300 |
| 2011/0001605 A1* | 1/2011 | Kiani | G06F 19/3418 340/5.6 |
| 2012/0007719 A1* | 1/2012 | Ida | H04W 24/10 340/10.4 |
| 2012/0084604 A1 | 4/2012 | Tamilio | |
| 2012/0116347 A1* | 5/2012 | Weinert | G06F 19/3456 604/504 |
| 2013/0095941 A1 | 4/2013 | Bentley et al. | |
| 2013/0211774 A1 | 8/2013 | Bentley et al. | |
| 2014/0121472 A1 | 5/2014 | Pinomaa | |
| 2014/0364701 A1 | 12/2014 | Masakov | |
| 2016/0058335 A1* | 3/2016 | Ashby | A61B 5/1118 600/301 |
| 2017/0000385 A1* | 1/2017 | Chen | A61B 5/1113 |

FOREIGN PATENT DOCUMENTS

| | | |
|---|---|---|
| WO | 2004072743 | 8/2004 |
| WO | 201004557 | 1/2010 |
| WO | 2010011621 | 1/2010 |
| WO | 2014195583 | 12/2014 |

* cited by examiner

302: controller
304: handshake component
306: processor
308: an application
310: memory
312: bank of detectors
314-316: detectors

FIG. 4

402: testing device
404: user device selecting component
406 – 412: user device connecting ports
414: diagnostic component
416: communication component
418: simulation selecting component
420 – 426: simulating modules
428: controlling device

FIG. 5

DEVICE AND METHODS FOR AUTOMATED TESTING

BACKGROUND

The present disclosure generally relates to devices and methods to test the functionality of a monitoring application.

There exists a need for a simpler way to test and verify the functionality of a monitoring application.

BRIEF SUMMARY OF THE DRAWINGS

The accompanying drawings, which are incorporated in and form a part of the specification, illustrate example embodiments and, together with the description, serve to explain the principles of the disclosure. In the drawings.

All Figures © Under Armour, Inc. 2016. All rights reserved.

DETAILED DESCRIPTION

Overview

In one aspect of the disclosure, a testing device configured to provide testing relating to at least one health parameter monitoring device and/or a health monitoring application configured to be run by at least one user device is disclosed. In one embodiment, the testing device comprises: at least one transceiver configured to receive a control signal from at least one controlling device; at least one health parameter monitoring device connection port configured to enable connection to and/or control of the at least one health parameter monitoring device; at least one user device connection port configured to enable connection to and/or control of the at least one user device; and a plurality of simulation apparatus configured to electronically recreate one or more physiological parameters of a user according to the control signal. The one or more physiological parameters are monitored by the at least one health parameter monitoring device, and the at least one health parameter monitoring device is configured to provide a plurality of data relating to the monitored electronically recreated physiological parameter to the at least one user device for entry within the health monitoring application. The at least one user device is further configured to output at least a display of the health monitoring application to the at least one controlling device for analysis thereof.

In another aspect of the disclosure a method of testing functioning of a health monitoring application and/or at least one health monitoring device is provided. In one embodiment, the method comprises: (i) connecting the at least one health monitoring device to a testing device; (ii) connecting at least one user device to the testing device, the at least one user device configured to execute a health monitoring application thereon; (iii) causing the at least one user device to execute the health monitoring application; (iv) receiving at the testing device a control signal from a controlling device, the control signal indicating at least one test to be run; (v) determining, based at least in part on the control signal, one or more of a plurality of simulation apparatus needed to accomplish the at least one test to be run; (vi) causing the one or more of the plurality of simulation apparatus to be controlled according to the control signal; and (vii) outputting to the controlling device data collected from the at least one health monitoring device and/or the health monitoring application during the test.

A third aspect of the present disclosure is drawn to a system for use with a user device and a controlling device, wherein the user device has a monitoring application stored thereon, wherein the monitoring application can monitor a parameter and generate parameter data associated with the monitored parameter and wherein the controlling device can transmit a controlling signal. In one embodiment, the system includes a connecting component, a diagnostic component, a communication component and a simulating module. The connecting component attempts a handshake with the phone. The diagnostic component outputs a failed handshake notification when the connecting component fails to handshake with the phone. The communication component receives the controlling signal. The simulating module simulates the monitored parameter based on the controlling signal.

A fourth aspect of the present disclosure is drawn to a method of testing a user device via a controlling device, wherein the user device has a monitoring application stored thereon, wherein the monitoring application monitors a parameter and generates parameter data associated with the monitored parameter and wherein the controlling device transmits a controlling signal. In one specific embodiment, the method includes: attempting, via a connecting component, a handshake with the user device; outputting, via a diagnostic component, a failed handshake notification when the connecting component fails to handshake with the user device; receiving, via a communication component, the controlling signal; and simulating, via a simulating module, the monitored parameter based on the controlling signal.

Exemplary Embodiments

Disclosed embodiments include systems, apparatus, methods and storage medium associated with automated device testing in general, and in particular enabling automated testing of various health-related activity monitoring devices.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

One of the recent trends in health and fitness is using a health parameter monitoring device to record data related to a health parameter of a user. The data can be downloaded directly to a receiving device, which can be a computer, smartphone, or other smart device, and the user can refer to the downloaded data to track his/her progress with regard to that health parameter. Alternatively, the health-parameter monitoring device may be further configured for analysis, such as where the monitoring device comprises a smartphone, for example. In one embodiment, the health-parameter monitoring device comprises a wearable device which incorporates various sensors used to determine activity levels of the wearer, such wearable devices include e.g., chest straps, arm or wrist bands, clothing, shoes, eyewear, headwear, etc. Non-limiting examples of such sensors include temperature sensors, pressure sensors, water sensors, moisture sensors, saline sensors, heart rate sensors, weight and/or body fat sensors, electric field sensors, current sensors, voltage sensors, impedance sensors, magnetic field sensors, accelerometers, altimeters, GPS sensors, magnetometers, optical sensors, and chemical sensors.

Additionally, other health-related applications have been developed which enable users to manually enter health-related data such as nutrition data, activity data, sleep data, etc. Moreover, the health-parameter monitoring devices may comprise other non-wearable devices such as e.g., smart scales, and other devices with which the user interacts to obtain health-related data.

In one specific embodiment, a user downloads a software application to a computing device, and then data is transmitted from the health-parameter monitoring device to the application on the computing device seamlessly after the user pairs the health-parameter monitoring device to the computing device. However, issues may arise when the application software, computing device software, and/or health-parameter monitoring device software is updated, causing problems with data transmission from the health parameter monitoring device to the computing device. In such instances, if any data is transferred, it may be corrupted and unusable. Additionally, there exists a need to test and verify the functionality of a monitoring application to avoid such data corruption.

System Architecture

Figure 1:
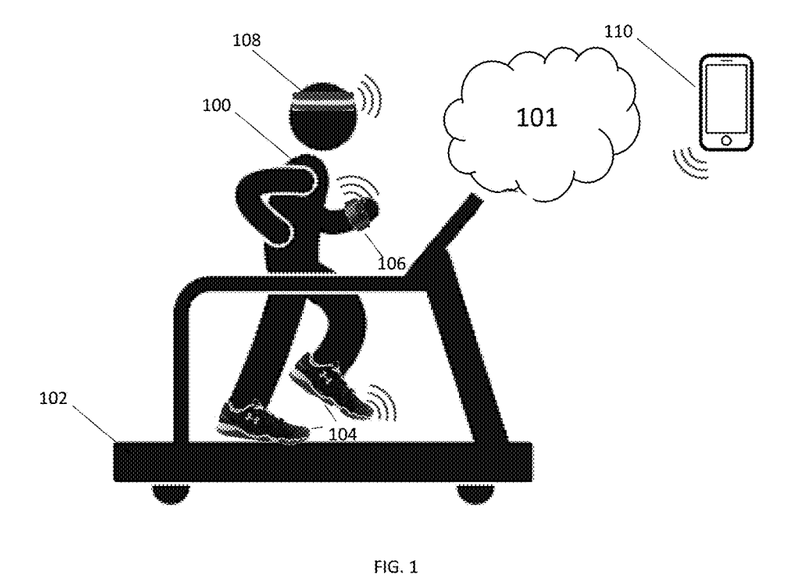
FIG. 1 is an illustrative rendering of one embodiment of a plurality of health parameter monitoring devices communicating with an exemplary user device.

FIG. 1 illustrates a plurality of health-parameter monitoring devices communicating with a user device.

Health-parameter monitoring devices generally comprise one or more portable computing devices designed to measure, sense, monitor, or otherwise receive biometric, environmental, and/or activity parameters. In one variant, health-parameter monitoring devices comprise wearable health-related parameter measurement and computing devices, such as e.g., a smart watch, an activity tracker, a heart rate monitor, a step tracking device, smart shoe(s), and/or smart eyeglasses (such as in the example of FIG. 1). In addition, a health-parameter monitoring device may comprise a smart phone having one or more of the foregoing capabilities and/or which enables manual entry of the foregoing parameters by the user thereof. Health-parameter monitoring devices may process data for more than one user profile as well.

Health-parameter monitoring devices generally monitor activity of the wearer/user. For example, an activity tracking device is configured to collect activity data such as steps taken, distance traveled, rate or pace of a run, and/or flights of stairs climbed, etc.; a heart rate monitor is configured to collect heartbeat data; a step tracking device collects data relating to a number of steps taken by the user/wearer; similarly smart shoes and smart eyeglasses may collect data relating to steps, distance, pace, and/or flights of stairs climbed. Furthermore, a smart watch and/or smart phone, may be utilized as an activity tracking device, a heart rate monitor, and/or step tracking device. In one embodiment, several individual health-parameter monitoring devices may be utilized by a single user during a given activity; for example, activity data may be collected from a user's smart phone, smart shoes and step tracking band.

User devices (or client devices) as discussed herein generally comprise stationary or portable computing apparatus which are configured to run a plurality of software applications thereon (as discussed in detail below) and/or access a web-based application. For example, a user device may comprise a desktop computer (such as those available from Dell Computing of Austin, Tex.), or smartphone, computing tablet, laptop computer, electronic reader, personal digital assistant, and so forth. Exemplary embodiments include e.g., Galaxy S4® from Samsung Electronics of Seoul, Korea, iPhone® or iPad® from Apple Computer of Cupertino, Calif.

In the specific example of FIG. 1, a user 100 is running on a treadmill 102. In one embodiment, the treadmill comprises a health parameter monitoring device (i.e., comprises a sensor). However, it is appreciated that the herein disclosed concepts may be utilized without fitness equipment (such as the treadmill 102) and/or with other types of user activity (such as weighing oneself on a scale, walking, sleeping, entering nutrition data, etc.). In the particular example of FIG. 1, the user 100 is using multiple health parameter monitoring devices including e.g., shoes 104, a smartwatch 106, and a headband 108 while running. In this embodiment, the treadmill 102, shoes 104, smartwatch 106, and headband 108 comprise one or more activity sensors which are in communication with a user device 110, via the network 101. In one example, the user device 110 may comprise a mobile or cellular phone, a tablet computer, a laptop computer, or any other device capable of receiving and sending information and having a processor (as discussed elsewhere herein).

The network 101 enables communication between the one or more health monitoring device(s), user device(s), and the computing devices of FIG. 2 (discussed below). The network 101 may comprise a wired and/or wireless, private and/or public network, including e.g., the Internet. Accordingly, each of the one or more health parameter monitoring device(s), user device(s) (and computing devices of FIG. 2) is configured with appropriate networking communication interfaces (not shown). An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, based stations, and so forth may be placed between the communication interfaces of foregoing devices.

The treadmill 102, shoes 104, smartwatch 106, and headband 108 all include sensors that are configured to detect parameters associated with the activities of the user 100 in one embodiment. As non-limiting examples, the treadmill 102 and/or shoes 104 may include force sensors to measure foot strike forces of the user 100, the smartwatch 106 may include a heart rate sensor to measure the heart rate of user 100, and the headband 108 may include moisture sensors to measure how much the user 100 is perspiring. It is appreciated however, that various other activity monitoring devices may be utilized consistent with the present disclosure including e.g., clothing, eyewear, etc. It is further appreciated the foregoing exemplary heath parameter monitoring devices may comprise any number and type of sensor and that the user 100 may utilize any number of the foregoing devices at one time; the referenced example being merely illustrative.

As the health parameter monitoring devices, e.g., the treadmill 102 shoes 104, smartwatch 106, and headband 108 in this embodiment, generate data via their respective sensors, the collected data is sent to the user device 110, where the user 100 can later view the data, such as by using a heath-monitoring application (see e.g., application 202 of FIG. 2) installed on the device 110.

Figure 2:
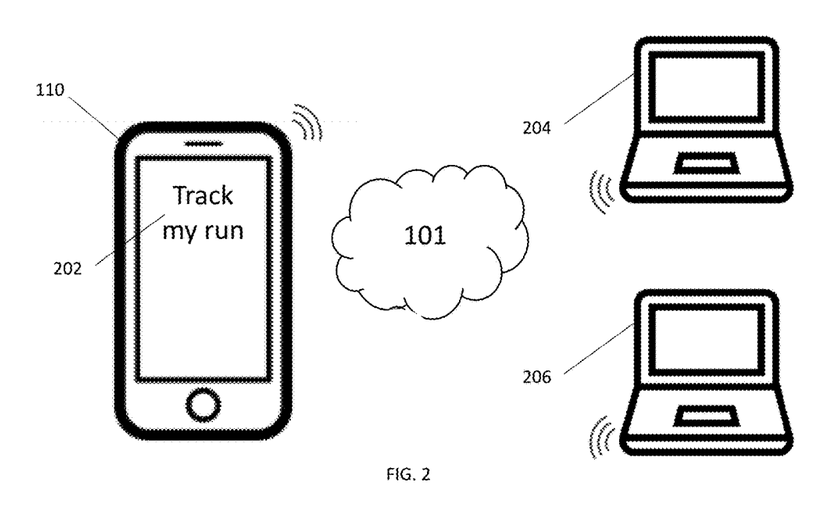
FIG. 2 is an illustrative rendering of one embodiment of an exemplary user device communicating with a plurality of exemplary computing devices via a network.

Referring now to FIG. 2, a user device communicating with a plurality of computing devices is illustrated.

As shown in FIG. 2, the user device 110 is configured to run a health monitoring application 202 thereon. Additionally, the user device 110 is in communication with at least two computing devices, computing device 204 and computing device 206, via the network 101.

In one exemplary embodiment, a user device 110 runs or is configured to access (such as via a web-browser) one or more heath-monitoring applications 202 such as e.g., UA Record™, MapMyFitness®, MyFitnessPal®, Endomondo®, etc. each owned by assignee hereof. Other health activity related monitoring applications 202 may additionally be utilized in connection with the present disclosure, such as those specifically designed to receive information from a particular health monitoring device. For example, an application which is published by a specific shoe sensor device manufacturer may be accessed by the user device 110. The foregoing application examples are merely representative of the general concepts of the present disclosure and are not to be considered limiting to the overall scope of the disclosure.

The user device 110 of the present embodiment includes an operating system and various applications, including e.g., the health monitoring application 202. For purposes of explanation, the health monitoring application 202 comprises a software application that monitors health-related activity or parameters. Operating systems are well known in the art as being preinstalled on user devices 110, and periodically requiring updates as new versions of the operating system are developed. To accomplish this, in one example, the computing device 204 communicates with the user device 110 to cause the update its operating system when new updates are available. In this example, the health monitoring application 202 does not come preinstalled on user device 110; rather, it must be installed by the user 100. The health monitoring application 202 may also require updates as new versions are developed. The computing device 206 communicates with the user device 110 and with the health monitoring application 202 to update the health monitoring application 202 when new updates are available. Similar logic applies to software updates at the health-parameter monitoring devices including e.g., the shoes 104, smartwatch 106, and headband 108.

Figure 3:
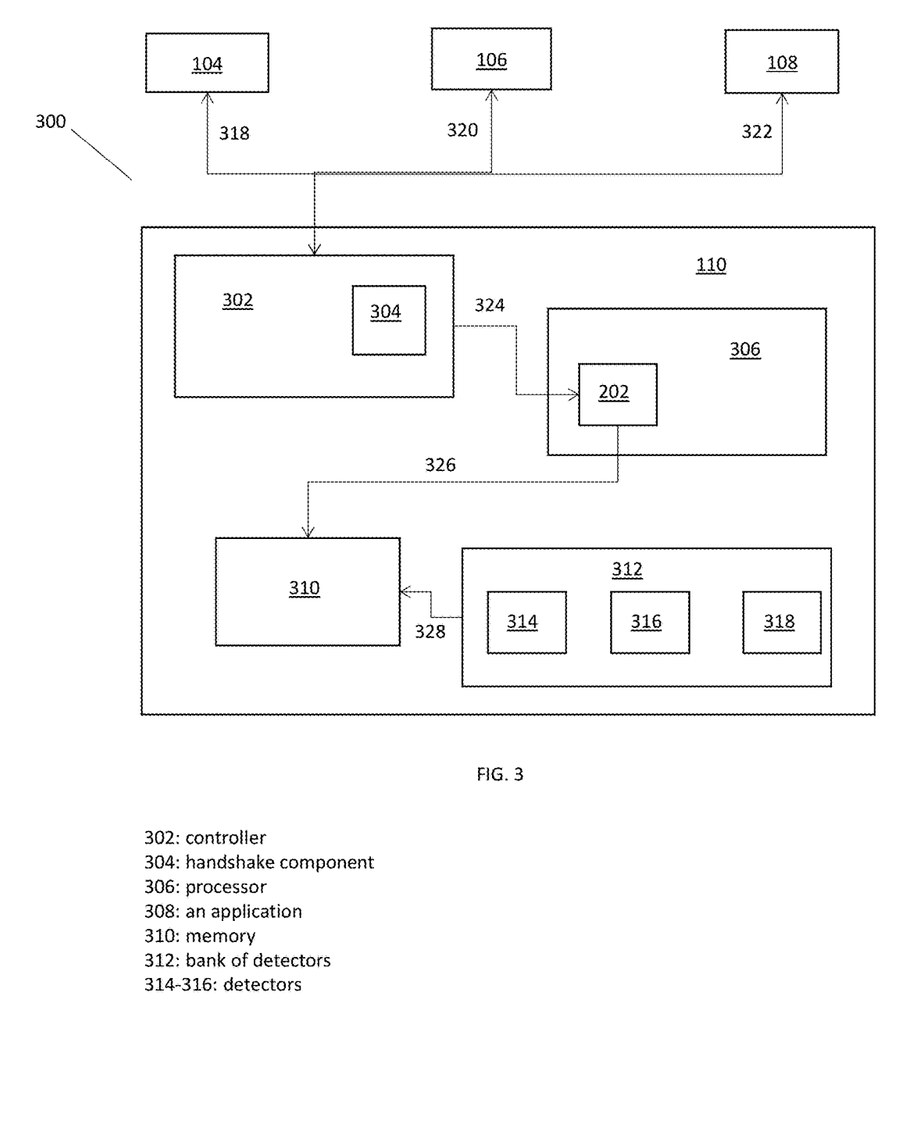
FIG. 3 is a block diagram illustrating an exemplary user device for use in collecting health parameter data from a plurality of health parameter monitoring devices.

FIG. 3 illustrates an exemplary user device to collect health parameter data from a plurality of health parameter monitoring devices.

As shown in the figure, the health parameter monitoring devices in this example include: the shoes 104, smartwatch 106, headband 108, and communicate to the user device 110. User device 110 generally includes a communication component 302, a processor 306, a memory 310, and a bank of detectors 312. Communication component 302 comprises a transceiver which includes a handshake component 304. The processor 306 is configured to run at least one computer application thereon, including the health monitoring application 202. Additionally, a bank of detectors 312 is provided in the user device 110, including detector 314, detector 316, and detector 318.

In the illustrated embodiment, the shoes 104, smartwatch 106, and headband 108 communicate with the communication component 302 via communication channels 318, 320, and 322 respectively. The communication component 302 additionally communicates with the health monitoring application 202 via a communication channel 324.

The health monitoring application 202 additionally communicates with the memory 310 via a communication channel 326. The memory 310 additionally communicates with the bank of detectors 312 via a communication channel 328.

As shown in the figure, the communication component 302, the processor 306, memory 310, and the bank of detectors 312 are shown as separate components. However, in some embodiments, at least two of the communication component 302, the processor 306, memory 310, and the bank of detectors 312 of may be incorporated as a single component.

The handshake component 304 assures that an open communication channel is established between the user device 110 and another device before any communication over the channel. The handshake component 304 may use any known method of handshaking that effectively opens communication between the user device 110 and another device. Non-limiting examples of handshaking include those performed via Wi-Fi, Bluetooth, a cellular network signal, or any combination thereof.

Detectors 314-318 may comprise any device or system that is operable to detect a parameter associated with an activity of a user (e.g., a monitored parameter). Non-limiting examples of detectors include accelerometers, magnetometers, temperature sensors, pressure sensors, heart rate monitors, touch sensors, altimeters, light sensors and gyroscopes.

In operation, and with reference to FIGS. 1-3, the user 100 owns the user device 110, and the user 100 loads the health monitoring application 202 onto the user device 110 to track health/fitness progress, such as when he/she exercises. To track progress properly, the user 100 pairs the heath parameter monitoring devices (e.g., the shoes 104) to the user device 110 so that the health monitoring application 202 running thereon can receive any data that, for example, the shoes 104 may collect while the user 100 is exercising (and wearing them).

Following the example above, using any known method to send a communication signal from shoes 104, the user 100 enables the shoes 104 to send a communication signal via the communication channel 318 to the handshake component 304 within the communication component 302. If there are no issues with the handshaking process, the shoes 104 are then paired to the user device 110. Similar logic relating to the pairing process applies to any health monitoring device and/or sensor including e.g., the smartwatch 106 and/or the headband 108; in this manner, each health parameter monitoring device is able to monitor parameters associated with the user.

Continuing the foregoing example, when the user 100 wants to track his/her activity (including e.g., sleep, nutrition, steps, workouts, weight, etc.), the user 100 opens the health monitoring application 202 on the user device 110 to begin acquiring data from any of the connected health monitoring devices (e.g., the treadmill 102, shoes 104, smartwatch 106 and/or headband 108). In some cases, the user 100 will not have to cause the health monitoring application 202 to open, rather the application 202 is opened automatically when the health monitoring device(s) are turned on, activated, or otherwise caused to generate data.

In another example, as the user 100 is running, the shoes 104 send data to the communication component 302, and the communication component 302 sends the data to the health monitoring application 202 within the processor 306. The health monitoring application 202 then displays the progress of the user 100 in real time on the screen of the user device 110, and the health monitoring application 202 can also send the data to the memory 310 to be stored for that user profile (i.e., user 100); in such instances the data may be viewed at a future time, and/or the data may be used to track the user's progress over time.

In addition, the detectors 314-316 may provide additional information about the performance of the user 100, and the data generated by the detectors 314-316 may be sent to the memory 310 via the communication channel 328.

Periodically, the operating system of the user device 110 is updated to address programming issues and/or to provide additional functionality. For example, returning to FIG. 2, the computing device 204 may update the operating system of the user device 110.

Similarly, the health monitoring application 202 may be periodically updated to address programming issues and/or to provide additional functionality. For example, the computing device 206 may update the application 202.

Updates to the operating system of user device 110 may have unintended detrimental consequences, such as for example, wherein the health monitoring application 202 fails to function properly. Non-limiting examples of such unintended detrimental consequences include instances where the health monitoring application 202 fails to function at all; the user device 110 is unable to handshake or connect to the health monitoring devices (such as the treadmill 102, shoes 104, smartwatch 106 or headband 108); and/or the health monitoring application 202 fails to function properly. For example, when the user 100 wants to record his/her progress after an operating system has been updated, the user 100 may find that the data is not available because e.g., the shoes 104 are no longer connected to the user device 110.

Similarly, updates to application 202 may result in similar unintended consequences.

Figure 4:
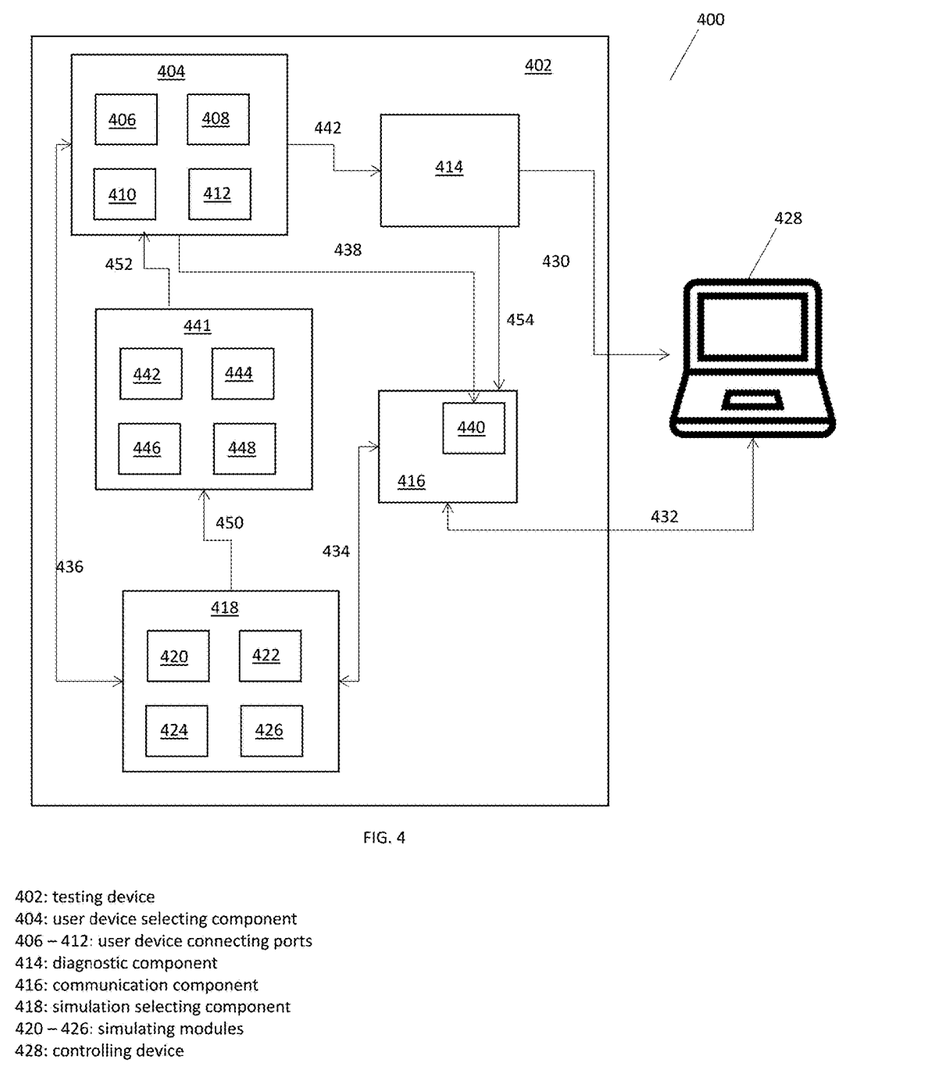
FIG. 4 is a block diagram illustrating an exemplary testing device configured to test the functioning of a health monitoring application and/or a health monitoring device.

FIG. 4 illustrates an exemplary testing device which is configured to test the functioning of a health monitoring application and/or a health monitoring device in accordance with aspects of the present disclosure.

As shown in the figure, a system 400 includes the testing device 402 and the controlling device 428. The testing device 402 includes a user device selecting component 404, a diagnostic component 414, a communication component 416, a simulation selecting component 418, and a health monitoring device selecting component 441.

In this example embodiment, the user device selecting component 404, the diagnostic component 414, the communication component 416, the simulation selecting component 418, and the health parameter monitoring device selecting component 441 are shown as independent components. However, in some embodiments, at least two of the user device selecting component 404, the diagnostic component 414, the communication component 416, the simulation selecting component 418, and the health parameter monitoring device selecting component 441 may be combined as a unitary component of the testing device 402.

Further, in some embodiments, at least one of the user device selecting component 404, the diagnostic component 414, the communication component 416, the simulation selecting component 418, and the health parameter monitoring device selecting component 441 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

The user device selecting component 404 includes a plurality of user device connecting ports, a sample of which are illustrated as user device connecting port 406, user device connecting port 408, user device connecting port 410 and user device connecting port 412. In one embodiment the user device comprises a mobile telephone; hence the testing device 402 is configured to connect to multiple different types of mobile telephones (e.g., iPhone, Galaxy, etc.) via individual ones of the given ports 406-412.

The communication component 416 includes an input port 440 which may be used for direct connection of the testing device 402 to another device (not shown).

The simulation selecting component 418 includes a plurality of simulating modules, a sample of which are illustrated as simulating module 420, simulating module 422, simulating module 424 and simulating module 426. In one embodiment, the simulation modules comprise modules which re-create or mimic human activity. For example, a simulation module may simulate a heartbeat, steps of a walk, a run, weighting activity, entry of nutrition activity (i.e., touch screen touches), etc. Moreover, the simulation modules may be configured to work simultaneously, thereby enabling the simulation selecting component 418 to select multiple modules to effect an entire simulation.

The health parameter monitoring device selecting component 441 includes a plurality of health parameter monitoring device connecting ports, a sample of which are illustrated as health parameter monitoring device connecting port 442, health parameter monitoring device connecting port 444, health parameter monitoring device connecting port 446, and health parameter monitoring device connecting port 448. As noted above, the health parameter monitoring devices may comprise e.g., smart watches, shoe sensors, heart rate sensors, and other sensor containing apparatus. The aforementioned ports 442-448 are configured to connect to individual ones of the given apparatus and/or sensors as discussed herein.

The controlling device 428 communicates with the diagnostic component 414 via a communication channel 430 and with the communication component 416 via a communication channel 432. The controlling device 428 generates instructions for simulations and provides those instructions to the communication component 416. The controlling device 428 also receives messages from the diagnostic component 414. In another embodiment, the controlling device 428 communicates with the components of the testing device 402 via the aforementioned network 101 (not shown). According to this embodiment, a remotely located controlling device 428 may control the testing device 402 over e.g., Ethernet and/or Internet connections.

In one variant, an operator at the controlling device 428 enters one or more commands to the testing device 402 which are intended to simulate a particular event. For example, the operator may elect to simulate a run, in such case, the operator may enter one or more commands at the controlling device 428 which cause the testing device 402 to select a user device via the user device selecting component 404, select one or more health monitoring devices via the health monitoring device selecting component 441, and utilize one or more of the simulation apparatus (via the simulation selecting component 418) to reenact the run. Continuing the example of simulating a run, the simulation selecting component 418 may select a heart rate monitor and a step or shoe sensor; the controller 428 provides commands which cause these devices to be stimulated to recreate the heartbeat of a person as he/she would begin a run, find a running pace, continue the pace for a given amount of time or distance, and completes the run by returning to a resting hear rate and walking pace.

In order to execute a test such as that described above, the communication component 416 communicates with the diagnostic component 414 via a communication channel 454. Additionally, the communication component 416 communicates with the user device selecting component 404 via a communication channel 438, with the simulation selecting component 418 via a communication channel 434.

As discussed above, the communication component 416 receives a signal from the controlling component 428 and sends the signal to simulation selecting component 418. In another embodiment, the input port 440 receives data from the user device selecting component 404 and provides the data to the controlling component 428.

Moreover, the simulation selecting component 418 communicates with the user device selecting component 404 via a communication channel 436 and with health parameter monitoring device selecting component 441 via a communication channel 450.

The simulating modules 420, 422, 424 and 426 receive instructions from the controller 428 (via the communication component 416) and execute the instructions to simulate parameters sensed and measured by a health parameter monitoring device and/or a user device. As noted above, a simulating module, for example simulating modules 420, 422, 424 and 426, may comprise any system or device that is able to simulate a parameter that is to be detected or monitored by a health parameter monitoring device, for example shoes 104, smart watch 106 and headband 108 or a smart phone. A non-limiting example of a simulating module may be an electromechanical device that periodically presses into the smart watch 106 in order to simulate a pulse of a user. For example, another non-limiting example of a simulating module may be an electromechanical device that periodically moves in a jolting manner to simulate the jarring motion of running, which may be detected by an accelerometer connected to one of the health parameter monitoring device connecting ports (not shown) and/or the sensor may be within e.g., the user device 110 and therefore connected via one of the user device connecting ports. In another non-limiting example, a simulating module may comprise an electrothermal device that changes temperature over time to simulate the user's temperature during a run, which may be detected by a thermocouple connected to one of the health parameter monitoring device connecting ports (not shown) and/or the thermocouple may be within e.g., a headband 108 also connected via one of the health parameter monitoring device connecting ports.

In order to effect the foregoing, the user device selecting component 404 communicates with the simulation selection component 418 via the communication channel 436, and communicates with the diagnostic component 414 via the communication channel 442, and with the input port 440 via the communication channel 438.

The user device selecting component 404 includes the user device connecting components 406, 408, 410 and 412. The user device connecting components 406, 408, 410 and 412 may include connectors that enable connection to any known type of user device. Non-limiting examples of user device connections included in user device connecting components 406, 408, 410 and 412 are micro-USB, USB, Lightning, or a wireless connection.

The health parameter monitoring device selecting component 441 communicates with simulation selecting component 418 via communication channel 450, and with user device selecting component 404 via communication channel 452.

The health parameter monitoring device connecting components 442, 444, 446, and 448 may include connectors that connect with known types of health parameter monitoring devices. Non-limiting examples of health parameter monitoring device connections included in health parameter monitoring device selecting components 442, 444, 446, and 448 are micro-USB, USB, Lightning, or a wireless connection.

The diagnostic component 414 additionally communicates with user device selecting component 404 via the communication channel 442. The diagnostic component 414 receives handshake information from the user device selecting component 404 and provides the handshake information to communication component 416. In addition, the diagnostic component 414 is configured to generate information relating to the monitored devices (e.g., the user device(s), sensor device(s), and/or health monitoring device(s) under test). For example, the diagnostic component 414 may report success and/or failure of individual ones of the user device, the health monitoring application, the sensors, and/or the health monitoring devices as e.g., a test run is executed (pursuant to commands by the controlling device 428).

The operation of system 400 will be further described with reference to FIG. 5.

Figure 5:
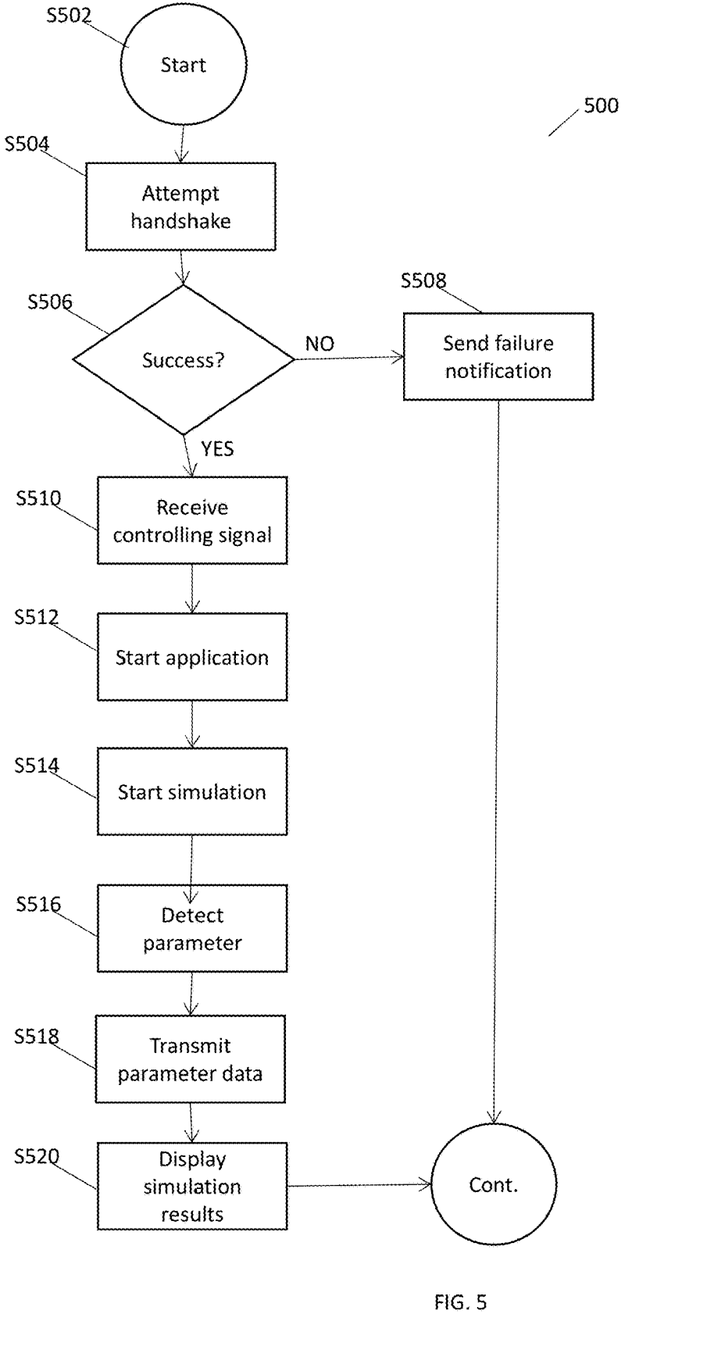
FIG. 5 is a logical flow diagram illustrating an exemplary method by which the function of a monitoring application and/or device is verified in accordance with aspects of the present disclosure.

FIG. 5 illustrates an exemplary method by which the function of a monitoring application is verified in accordance with aspects of the present disclosure.

As shown in the figure, method 500 starts (S502) and a handshake is attempted (S504).

Assume for example that a testing device operator is made aware that one or more user device manufacturers have updated their operating systems, that one or more health parameter monitoring device manufacturers have updated their hardware and/or software, and/or that an application that communicates with the health parameter monitoring device (i.e., a health monitoring application) has been updated. Thus, the operator tests the updated operating systems, software, hardware, and/or application to ensure that the updates have not negatively impacted the ability of the user devices to receive and display parameter data from the health parameter monitoring devices, and/or the ability of the health parameter devices to collect data and transmit the data to the user devices.

To begin the testing process, the operator connects user devices to user device connecting ports 406 and 408 of user device selecting component 404 and health parameter monitoring devices to health parameter monitoring device connecting ports 442 and 444 of health parameter monitoring device selecting component 441.

The first test is to determine if a handshake between each user device can be made with a health parameter monitoring device (S504). In this example, suppose the operator wishes to connect a first health parameter monitoring device to the first health parameter monitoring device connecting port 442, which is then connected to a first user device connected to the first user device connecting port 406. Further, suppose the operator wishes to connect a second health parameter monitoring device to a second health parameter monitoring device connecting port 444, which is then connected to the second user device connected to the second user device connecting port 408. The first and second health parameter monitoring devices send handshake signals to the phone selecting component 404 via communication channel 452, and the handshake signals are routed via the appropriate first and second user devices via their respective user device connecting ports.

Returning to FIG. 5, the system determines whether the handshakes were successful (S506).

When the handshake signal sent by user device connecting component 404 is not successful (NO at S506), then a failure notification is sent (S508). In one specific embodiment, when the handshake is unsuccessful, the user device selecting component 404 sends a signal regarding the unsuccessful handshake to the diagnostic component 414. The diagnostic component 414 then sends the handshake information to the communication component 416, which sends the handshake information to the controlling device 428 to notify the controlling device 428 that the handshake was unsuccessful.

Returning to FIG. 5, after the failure notification is sent (S508), method 500 continues (S522). In such a situation, the testing device operator is made aware that the update (such as to the user device operating system, to the health monitoring device, and/or to the health monitoring application) does not enable the user device to handshake with the health parameter monitoring device. Accordingly, the testing device operator may address the issue.

Returning to S506, in the event that the handshake signal sent by user device connecting component 404 is successful in connecting the health parameter monitoring device connected to health parameter monitoring device connecting component 441 to the user device connected to user device connecting component 404 (YES at S506), then a controlling signal is received (S510).

In other words, the testing device operator provides a controlling signal from the controlling device 428 to control the simulating module. The controlling device 428 then sends the controlling signal to the communication component 416, and the communication component 416 provides the controlling signal to the simulation selecting component 418.

The controlling signal from the controlling device 428 includes information instructing the simulation selecting component 418 to enable appropriate instantiation of one or more of the simulating modules 420, 422, 424 and 426. The controlling signal also includes information instructing which parameters should be enabled by the simulating modules 420, 422, 424 and 426, and in which way the parameters should be enabled. For example, consider the non-limiting example situation where the testing device 402 is arranged to test an application on the user device 110 in conjunction with a smartwatch 106. To assess the ability of the user device 110 to communicate with the smartwatch 106 and receive parameter data appropriately, the operator desires to test a plurality of parameters which the smartwatch 106 should be able to detect. To do so, the controlling signal enables simulating the modules 420, 422, 424 and 426 to simulate a user going for a 5-mile run. To simulate a 5-mile run, the controlling signal instructs a heart rate simulating apparatus (not shown) connected via the simulating module 420 to provide simulated heart beats to the smartwatch 106 by pushing on the smartwatch 106 in a pulsing manner. The controlling signal may also instruct an actuator apparatus (not shown) connected via the simulating module 422 to provide simulated steps to the smartwatch 106 by imparting a jarring force to the smartwatch 106 that would correspond to the force encountered as a user's foot strikes the ground during a run. The controlling signal may further instruct a simulation apparatus to provide a simulated perspiration to a sensor of the smartwatch 106 by causing the simulating apparatus to coat a surface of the smartwatch 106 sensor in liquid (such as water or saline) similar to how a user would sweat during a 5-mile run.

Returning to FIG. 5, when the handshake is a success (S506) and the controlling signal is received (S510), the health monitoring application is started (S512).

In one specific embodiment, the health monitoring application is pre-loaded on the user device which is connected to user device connecting component 408. Starting the application may be accomplished by an operator who is physically present at the testing device 402 pressing the application icon on the screen of the user device, but it may also be started from an initiation signal sent from the controlling device 428.

Returning to FIG. 5, after the application is started (S512), the simulation is started (S514).

The simulating modules 420, 422, 424 and 426 execute the controlling signal and simulate a user going for a 5-mile run as discussed above. More specifically, the controlling signal may simulate the user running at progressively faster speeds for each mile, or until a running pace is met, thereafter the running pace is kept until 5 miles have been reached.

A heart beat simulating apparatus at the simulating module 420 in one specific example, may periodically push on the smartwatch 106 to simulate a pulse rate of 90 beats per minute (bpm) for the first mile, 95 bpm for the second mile, 100 bpm for the third mile, 105 bpm for the fourth mile, and 110 bpm for the fifth mile. An actuator apparatus at the simulating module 422 in one specific example, may impart jarring forces to the smartwatch 106 to simulate a foot strike force of 1.5 times the user's body weight (1.5×BW) during the first mile, 1.7×BW during the second mile, 1.9×BW during the third mile, 2.1×BW during the fourth mile, and 2.3×BW during the fifth mile. A simulation apparatus at the simulating module 426 may expose smartwatch 106 to a certain amount of liquid for the first mile and increase that amount of liquid for each additional mile to indicate the user is perspiring more as he is running at a faster speed.

In another embodiment, the simulating modules 420, 422, 424 and 426 provide the simulated parameters to the smartwatch 106 through electrical signals rather than through mechanical means. For example, the simulating module 420 may "trick" the smartwatch 106 into detecting the pulse rate described above by providing the smartwatch 106 the data associated with the pulse rates rather than physically manipulating the smartwatch 106 such that the smartwatch 106 detects the pulse rates via its sensors (as occurs in the examples given above).

However the smartwatch 106 receives the data associated with the 5-mile run, the smartwatch 106 provides the data associated with the run to the user device selecting component 404. More specifically, in this example the smartwatch 106 provides the data associated with the run to the user device connecting component 408, which is connected to the user device 110.

After the simulation is started (S514), one or more parameters are detected (S516).

In one embodiment, the user device 110 detects the signals sent by the smartwatch 106 (or other health parameter monitoring device) indicating that the user completed a 5-mile run at varying speeds. The user device also generates parameter data based on the signals sent by the smartwatch 106 (or other health parameter monitoring device). The parameter data generated by user device 110 may include the raw data associated with the user's pulse rate, foot strike force, running speed, perspiration, etc. The parameter data generated by user device 110 may also include functions of the raw data transmitted by smartwatch 106 (or other health parameter monitoring device).

Returning to FIG. 5, after the parameter is detected (S516), the parameter data is transmitted (S518).

The parameter data gathered by the user device 110 is transmitted to the input port 440 of the communication component 416, and the communication component 416 transmits the parameter data to the controlling device 428 in one embodiment.

After the parameter data is transmitted (S518), the results of the simulation are displayed (S520).

The parameter data gathered by the user device 110 is displayed on the controlling device 428. If the updates to the operating system of the user device 110, health monitoring device, and/or the to the application did not interfere with the parameter data acquisition or the parameter data generation, the controlling device 428 will display information that exactly matches the simulated run of the controlling signal sent by the controlling device 428 to the simulating module 422.

If the updates did interfere with the data acquisition or the parameter data generation, the controlling device 428 will not display information that exactly matches the simulated run. For example, the controlling device 428 may display data showing that the user ran 15 miles at a single speed, or that the user did not run at all. In any case, if the information displayed on the controlling device 428 does not exactly match the simulated run of the controlling signal, the operator must take action to assure the issue is fixed.

Figure 6:
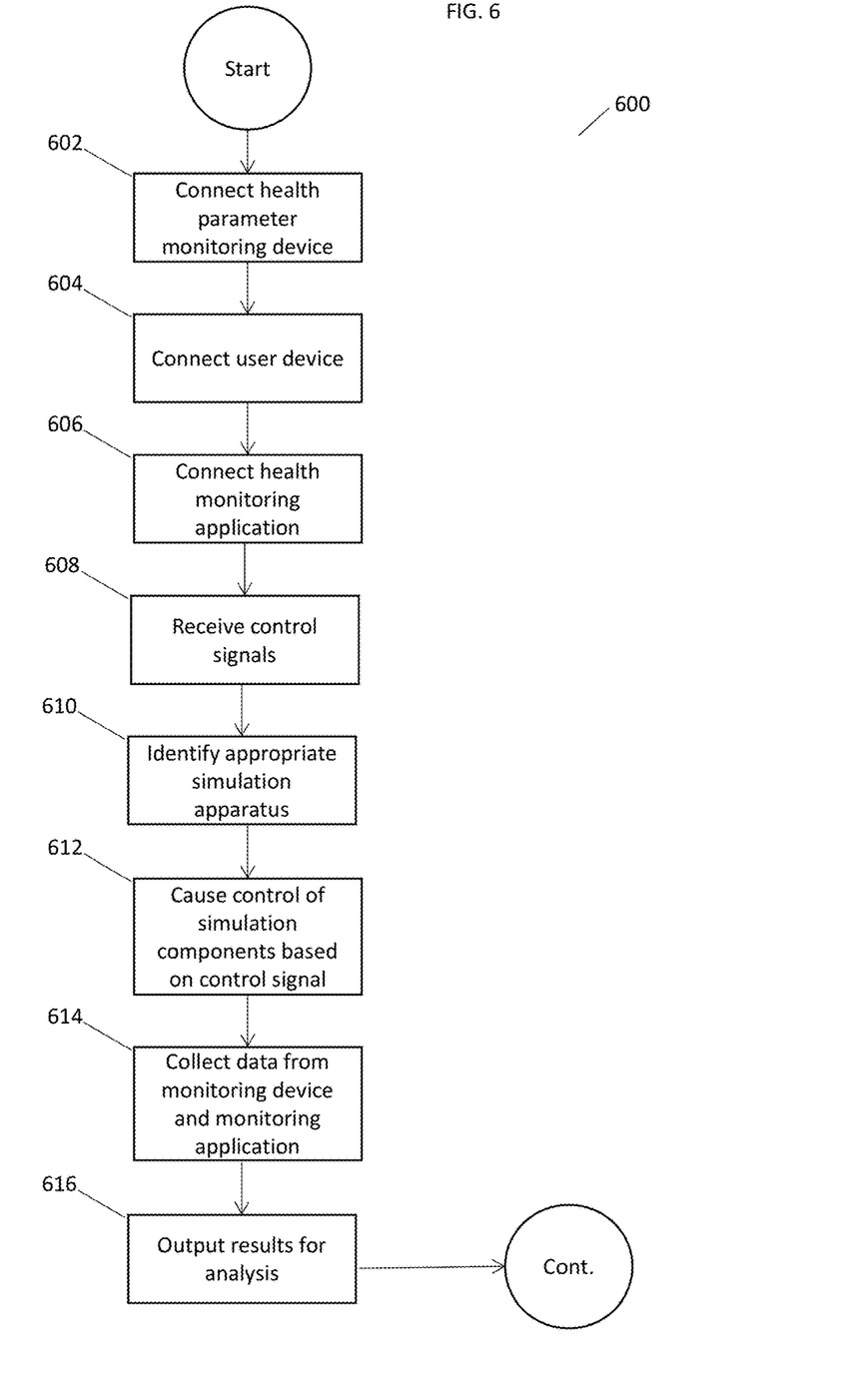
FIG. 6 is a logical flow diagram illustrating another exemplary method for testing the functioning of a health monitoring application and/or a health monitoring device.

Referring now to FIG. 6, another exemplary method 600 for testing the functioning of a health monitoring application and/or a health monitoring device is given.

As shown, per step 602, one or more health parameter monitoring devices are connected to the testing device 402. As noted above, the health parameter monitoring devices may comprise a smart watch, smart phone, headband, eye wear, heart rate monitor, sleep monitor, or other device configured to sense, collect, receive and/or otherwise obtain data relating to one or more health parameters of a user. The health parameter monitoring devices are connected to the testing device 402 via one or more of the health parameter monitoring device connecting ports 442-448 of the health parameter monitoring device selecting component 441.

Next, at step 604, one or more user devices are connected to the testing device 402. As noted above, the user devices may comprise a smart phone, a mobile telephone, a laptop computer, a tablet computer, a personal computer, and/or any computerized device having a processor and configured to run or access at least one health monitoring application thereon. The user devices are connected to the testing device 402 via one or more of the user device connecting ports 406-412 of the user device selecting component 404.

Per step 606, a health monitoring application is connected to the system. In one embodiment connection of the heath monitoring application comprises opening or starting the application (i.e., causing it to be run) at one or more of the connected user devices. In another embodiment, the application is run at a separate device (such as the controller 428) or other remote entity, and/or accessed by a connected one of the user devices.

It is noted that one or more of the aforementioned connection steps (602-606) may further comprise the so-called "handshake discussed elsewhere herein.

Next, at step 608, one or more control signals are received at the testing device 402 from the controlling device 428. As discussed herein, the control signals provide one or more executable steps to be taken at the testing device 402 with respect to the devices under test (e.g., the one or more user devices and/or the one or more health parameter monitoring devices. The control signals identify one or more simulation modules which are necessary to accomplish the test or simulation. Hence, at step 610, the appropriate simulation apparatus are identified from the control signals.) The one or more of the plurality of simulation modules 420-426 are selected via the simulation selecting component 418, in one embodiment.

At step 612, the one or more identified simulation modules are controlled based on the control signal. For example, the control signal may indicate that a heart rate of 90 bpm is needed for 3 minutes, followed by a heart rate of 110 bpm for 5 minutes, then a heart rate of 95 bpm for 6 minutes, followed by a heart rate of 90 bpm for 4 minutes. Accordingly, a heart rate simulation module performs the necessary pulses or beats to meet the control signal requirements.

Per step 614, data is collected from the health parameter monitoring devices and the health monitoring application; the results of the data collection are then output for analysis at step 616. In one embodiment, as the simulation is executed, the health parameter monitoring devices sense the simulated activity and convert the activity into e.g., heart rate data. The collected and converted activity is then provided to the health monitoring application which is configured to display the data in a format easily understood by a user. In one variant, the raw data provided to the user device (to be used by the health monitoring application) is further outputted to the controlling device 428. In addition, or in the alternative, the controlling device 428 is configured to mirror the display of the user device such that as the health monitoring application transitions the data to a format which is easily understood by the user, the operator at the controlling device 428 sees the same output data. As discussed herein, the output to the controlling device 428 is compared to the originally provided control signal to determine whether the health parameter monitoring device, health monitoring application and/or user device are working appropriately.

The above described embodiments of the disclosure relate to a system and method to test the effects of monitoring application, device, and/or operating system updates on the interaction between a health parameter monitoring device and a user device to which it was paired before the updates (including e.g., when a new device is added to the system). The system tests the ability of a health parameter monitoring device to complete a handshake with a user device after an update. The system also tests the ability of the application to correctly detect the information provided by the health parameter monitoring device after an update by simulating typical activities a user would perform.

The foregoing description of various preferred embodiments have been presented for purposes of illustration and description. It is not intended to be exhaustive or to limit the disclosure to the precise forms disclosed, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

What is claimed as new and desired to be protected by Letters Patent of the United States is:

1. A testing device configured to provide testing relating to at least one tested device, said tested device comprising: (i) at least one health parameter monitoring device and (ii) at least one user device configured to run a health monitoring application, and said testing comprising testing of generation of a display by said at least one health monitoring device and said at least one user device, said testing device comprising:
   at least one transceiver configured to receive a control signal from at least one external controlling device;
   at least one health parameter monitoring device physical connection port configured to enable connection of said testing device to said at least one health parameter monitoring device;
   at least one user device physical connection port configured to enable connection of said testing device to said at least one user device; and
   a plurality of simulation apparatus configured to electronically recreate one or more physiological parameters of a user according to said control signal;
   wherein said at least one health parameter monitoring device is configured to monitor said one or more electronically recreated physiological parameters provide a plurality of data relating to said monitored electronically recreated physiological parameters to said at least one user device for entry within said health monitoring application; and
   wherein said testing comprises analysis of an output of a display of said health monitoring application by said at least one user device.

2. The testing device of claim 1, further comprising at least one diagnostic component configured to analyze said connection between said testing device and said at least one health parameter monitoring device via said at least one health monitoring device physical connection port and said connection between said testing device and said at least one user device via said at least one user device physical connection port; results of said analysis being output to said at least one external controlling device for further analysis of said results.

3. The testing device of claim 1, wherein said at least one user device comprises a plurality of smart phone devices, each of said plurality of smart phone devices having a unique operating system executed thereon.

4. The testing device of claim 3, wherein each of said plurality of smart phone devices is configured to receive said plurality of data relating to said monitored electronically recreated physiological parameters and to derive a display of said monitored electronically recreated physiological parameters with said health monitoring application.

5. The testing device of claim 1, wherein said at least one external controlling device provides said control signal via communication to said testing device using one or more of: Wi-Fi, Bluetooth, a cellular network, a multicast wireless sensory network, and/or combinations thereof.

6. The testing device of claim 1, wherein said plurality of simulation apparatus comprise electromechanical devices operable to receive an electrical signal and to provide a mechanical motion based on said electrical signal.

7. The testing device of claim 1, wherein said at least one health parameter monitoring device comprises at least one of: a smart phone, a smart watch, a smart scale, a step or activity counter, a sleep monitor, and/or a heart rate monitor.

8. A method of testing data collection functioning of: (i) a health monitoring application run at a user device and (ii) at least one health monitoring device, said method comprising:
   connecting said at least one health monitoring device to a testing device;

connecting at least one user device to said testing device, said at least one user device configured to execute said health monitoring application at a processor of said at least one user device;

causing said at least one user device to execute said health monitoring application;

receiving at said testing device a control signal from an external controlling device, said control signal indicating at least one test to be run;

determining, based at least in part on said control signal, one or more of a plurality of simulation apparatus needed to accomplish said at least one test to be run;

causing said one or more of said plurality of simulation apparatus to be controlled according to said control signal;

outputting to said external controlling device data collected from said at least one health monitoring device and/or said health monitoring application during said at least one test; and monitoring said output to inform a result of said testing of said data collection functioning.

9. The method of claim 8, wherein said connection of said at least one health monitoring device and/or said at least one user device to said testing device further comprises verification via a diagnostic apparatus of said testing device.

10. The method of claim 8, wherein said control signal indicating said at least one test to be run comprises a signal which provides specific instructions to individual ones of said plurality of simulation apparatus detailing a particular physiological parameter to be recreated by said individual ones of said plurality of simulation apparatus.

11. The method of claim 8, wherein said external controlling device provides said control signal via communication to said testing device using one or more of: Wi-Fi, Bluetooth, a cellular network, and a multicast wireless sensory network.

12. The method of claim 8, wherein said output of said data collected from said at least one health monitoring device during said at least one test comprises raw data relating to one or more health parameters monitored by said at least one health monitoring device.

13. The method of claim 12, wherein said at least one health monitoring device comprises at least one of: a smart phone, a smart watch, a smart scale, a step or activity counter, a sleep monitor, and/or a heart rate monitor; and
wherein said raw data comprises at least one of: step data, activity data, accelerometer data, weight data, sleep data, and/or heart beat data.

14. The method of claim 8, wherein said output of said data collected from said health monitoring application during said at least one test comprises an output of a display generated by said monitoring application at said external controlling device.

15. A method of testing data collection functioning of a phone via an external controlling device, said phone having a monitoring application stored at a storage apparatus of said phone, said monitoring application being operable to monitor a parameter and to generate parameter data associated with said monitored parameter, said method comprising:
establishing communication between said external controlling device, said phone, and a simulating apparatus;
said external controlling device transmitting a controlling signal which is received at a communication component of said simulating apparatus, said controlling signal causing said simulating apparatus to simulate said parameter, said simulated parameter being monitored by said monitoring application of said phone;
causing said monitoring application to output data relating to said monitored simulated parameter to said external controlling device; and
monitoring said output data to inform a result of said testing of said data collection functioning.

16. The method of claim 15, wherein said phone comprises a first operating system, and wherein said method further comprises:
establishing communication between said external controlling device and a second phone, said second phone comprising a second operating system and having a second monitoring application stored at a storage apparatus of said second phone; and
said external controlling device causing a second simulating apparatus to simulate a second parameter, said second parameter being monitored by said second monitoring application.

17. The method of claim 15, wherein said communication comprises at least one of: a Wi-Fi signal, a Bluetooth signal, a cellular network signal, and a multicast wireless sensory network signal.

18. The method of claim 15, wherein said causing said simulating apparatus to simulate said parameter comprises utilizing an electromechanical device that is configured to receive an electrical signal and is operable to provide a mechanical motion based on said electrical signal.

19. The method of claim 15, wherein said causing said simulating apparatus to simulate said parameter comprises utilizing a thermoelectric device that is operable to receive an electrical signal and that is operable to output heat based on said electrical signal.

20. The method of claim 15, wherein said external controlling device is remote to said phone yet in communication with said phone via a network.

* * * * *